United States Patent
Hagedorn et al.

(10) Patent No.: US 10,335,512 B2
(45) Date of Patent: Jul. 2, 2019

(54) DERMAL FILLER BASED ON CROSSLINKED HYALURONIC ACID AND CARBOXYMETHYL CELLULOSE LUBRICANT

(71) Applicant: MERZ PHARMA GMBH & CO. KGAA, Frankfurt am Main (DE)

(72) Inventors: Nadine Hagedorn, Frankfurt am Main (DE); Roland Stragies, Berlin (DE); Franck Villain, Paris (FR); Lubin Belkovi, Friedrichsdorf (DE); Radia El-Banna, Bad Vilbel-Gronau (DE)

(73) Assignee: MERZ PHARMA GMBH & CO. KGAA, Frankfurt am Main (DE)

( * ) Notice: Subject to any disclaimer, the term of this patent is extended or adjusted under 35 U.S.C. 154(b) by 0 days.

(21) Appl. No.: 15/526,460

(22) PCT Filed: Nov. 12, 2015

(86) PCT No.: PCT/EP2015/002270
§ 371 (c)(1),
(2) Date: May 12, 2017

(87) PCT Pub. No.: WO2016/074794
PCT Pub. Date: May 19, 2016

(65) Prior Publication Data
US 2017/0333596 A1 Nov. 23, 2017

(30) Foreign Application Priority Data
Nov. 13, 2014 (EP) .................................... 14003829

(51) Int. Cl.
| A61L 27/26 | (2006.01) |
| A61L 27/20 | (2006.01) |
| A61L 27/52 | (2006.01) |
| C08L 5/08 | (2006.01) |
| C08B 37/08 | (2006.01) |
| A61L 27/58 | (2006.01) |

(52) U.S. Cl.
CPC .............. *A61L 27/26* (2013.01); *A61L 27/20* (2013.01); *A61L 27/52* (2013.01); *A61L 27/58* (2013.01); *C08B 37/0072* (2013.01); *C08L 5/08* (2013.01); *A61L 2400/06* (2013.01)

(58) Field of Classification Search
None
See application file for complete search history.

(56) References Cited

U.S. PATENT DOCUMENTS

| 6,558,612 | B1* | 5/2003 | Hubbard | A61F 2/0036 264/654 |
| 8,450,475 | B2 | 5/2013 | Lebreton | |
| 9,371,402 | B2* | 6/2016 | Chen | C08B 37/0072 |
| 2007/0212385 | A1* | 9/2007 | David | A61K 8/02 424/422 |
| 2010/0004700 | A1* | 1/2010 | Alleyne | A61K 9/0085 606/86 R |
| 2010/0172829 | A1* | 7/2010 | Anderson | A61L 27/446 424/1.11 |
| 2012/0095206 | A1 | 4/2012 | Chen et al. | |
| 2012/0172328 | A1* | 7/2012 | Lebreton | A61K 8/42 514/54 |
| 2014/0235547 | A1* | 8/2014 | Mithieux | A61K 38/39 514/18.8 |
| 2016/0074519 | A1* | 3/2016 | Khabarov | C08B 37/0072 514/249 |

FOREIGN PATENT DOCUMENTS

| EP | 2236523 A1 | 10/2010 |
| KR | 2009-0043973 A | 5/2009 |
| WO | 2014/056723 A1 | 4/2014 |
| WO | 2014/172784 A1 | 10/2014 |

OTHER PUBLICATIONS

BioForm, Radiesse Technical Data Sheet, 2004. (Year: 2004).*
International Search Report Dated of PCT/EP2015/002270 dated Jan. 13, 2016.

* cited by examiner

*Primary Examiner* — Dale R Miller
(74) *Attorney, Agent, or Firm* — McBee Moore Woodward & Vanik IP, LLC

(57) ABSTRACT

The present invention relates to injectable dermal filler compositions in the form of a gel, comprising hyaluronic acid (HA), carboxymethyl cellulose (CMC) and, optionally, microparticles such as calcium hydroxyapatite (CaHAP) microparticles. The injectable dermal filler compositions have improved rheological properties while at the same time have low extrusion forces. The present invention further relates to a method for preparing such injectable dermal filler compositions and their use for cosmetic and therapeutic purposes.

14 Claims, 4 Drawing Sheets

DERMAL FILLER BASED ON CROSSLINKED HYALURONIC ACID AND CARBOXYMETHYL CELLULOSE LUBRICANT

CROSS REFERENCE TO RELATED APPLICATIONS

This application is a § 371 National Stage Application of PCT/EP2015/002270, filed 12 Nov. 2015, which claims priority to EP 14003829.0 filed 13 Nov. 2014 and EP 15000338.2 filed 5 Feb. 2015.

FIELD OF THE INVENTION

The present invention relates to injectable dermal filler compositions in the form of a gel, comprising crosslinked hyaluronic acid (HA), carboxymethyl cellulose (CMC) and, optionally, microparticles such as calcium hydroxyapatite (CaHAP) microparticles. The injectable dermal filler compositions have improved rheological properties while at the same time have low extrusion forces. The present invention further relates to a method for preparing such injectable dermal filler compositions and their use for cosmetic and therapeutic purposes.

BACKGROUND OF THE INVENTION

It is a common desire to achieve and preserve a youthful appearance as a common denominator of beauty. Over time, however, the skin starts lose its youthful appearance, especially in the face. The most common esthetic signs of facial aging include visibility of skin wrinkles, deep nasolabial folds, glabellar lines, marionette lines, buccal commissures, and perioral wrinkles.

These aging changes are often treated by the injection of dermal fillers to increase the tissue volume. Currently, there are numerous dermal fillers available, which can be broadly classified into two categories. The first category of fillers provides a long-term effect by creating volume and includes fillers such as crosslinked hyaluronic acid (HA) fillers. The second category of fillers provides a long-term effect by inducing neocollagenesis. The best-known and widely used example is Radiesse®, which comprises calcium hydroxyapatite microspheres, a gel carrier of carboxymethyl cellulose (CMC) and glycerin.

Ideal dermal fillers should be biocompatible, have a low adverse event profile, and provide a reasonably long-lasting persistence (longevity), an effective volumizing capacity and ease of injection. HA-based fillers offer many of these desirable properties of dermal fillers. Since HA is found in almost all species, it has no antigenicity and exhibits excellent tolerance. Furthermore, the crosslinking of HA allows the production of crosslinked HA products that have a good lifting capacity and are stable for more than 12 months up to two years.

A major drawback of HA-based fillers is, however, that they are often difficult to inject. For this reason, non-crosslinked HA ("free" HA) is commonly added as a lubricant to ease injection. Unfortunately, the desired decrease of extrusion force that is caused by the addition of free HA compromises other desirable physical properties of the gel. In particular, the G Prime (G') parameter is lowered, thereby resulting in a reduced volumizing effect, and the dynamic viscosity is decreased.

Radiesse® is a dermal filler that also provides desirable characteristics of a dermal filler, including acceptable longevity, biocompatibility, and a good capacity to create volume. When injected, the small calcium hydroxyapatite microspheres act as a scaffold that promotes new tissue formation similar to its surrounding environment. However, since the CMC carrier of Radiesse® is quickly absorbed in vivo (in about 3 months), there is a potential and transient decrease of the filling effect since neocollagenesis may not be synchronized with CMC elimination. Furthermore, there is no antidote (reversal agent) available for CMC that would allow for a partial correction after filler application.

European patent No. 1 080 698, filed in 1993, discloses an injectable soft tissue augmentation material comprising finely divided ceramic particles (e.g., CaHA) and covers inter alia, Radiesse®. In addition, WO 2014/056723 describes a viscoelastic gel comprising crosslinked HA at a concentration of between 1% and 4% (w/v) and hydroxyapatite particles at a concentration of between 10% and 70% (w/v).

OBJECT OF THE INVENTION

In view of the above, the object of the present invention is to provide a long-lasting dermal filler composition having improved rheological properties while at the same time being easily injectable.

SUMMARY OF THE INVENTION

The above object is solved by the provision of an injectable dermal filler composition in the form of a gel that makes use of carboxymethyl cellulose as a lubricant. This new type of dermal filler offers good longevity, is easily injectable and has improved rheological properties (i.e. G Prime (G') and dynamic viscosity) resulting in an excellent ability to create volume.

In a first aspect, the present invention provides an injectable dermal filler composition in the form of a gel, comprising crosslinked (e.g., BDDE crosslinked) hyaluronic acid (HA) and carboxymethyl cellulose (CMC).

The crosslinked HA is usually present in a concentration of 0.1% to 4.0% weight/volume (e.g., 0.5% to 4.0% or 1.0% to 4.0% weight/volume) and provides a crosslinked matrix, whereas the CMC is usually present in a concentration of 1.0% to 25% volume/volume and is added as a lubricant/lubricant phase. In a preferred embodiment, the injectable dermal filler composition further comprises resorbable biocompatible microparticles, in particular calcium hydroxyapatite microparticles.

In a second aspect, the present invention provides a kit comprising the injectable dermal filler composition according to the first aspect of the invention.

In a third aspect, the present invention provides a method for preparing an injectable dermal filler composition according to the first aspect of the present invention, comprising the following steps:
 (a) providing a crosslinked hyaluronic acid gel,
 (b) providing a carboxymethyl cellulose gel,
 (c) mixing the crosslinked hyaluronic acid gel and the carboxymethyl cellulose gel.

In a fourth aspect, the present invention relates to the use of an injectable dermal filler composition according to the first aspect of the invention or of the kit according to the second aspect of the invention for cosmetic applications such as treatment of facial lines.

In a fifth aspect, the present invention provides an injectable dermal filler composition according to the first aspect of the invention or of a kit according to the second aspect of the invention for use in therapy, in particular for use in treating stress urinary incontinence, vesico-ureteral reflux, vocal fold insufficiency, and vocal fold medialization.

In a sixth aspect, the present invention provides a method for replacing or filling of a biological tissue or increasing the volume of a biological tissue, comprising administering to a subject in need thereof an effective amount of the injectable dermal filler composition according to the first aspect of the invention.

Particular embodiments of the present invention are set forth in the appended claims.

Additional objects, advantages and features of the present invention will become apparent to those skilled in the art in view of the following detailed description of the invention, the drawings and the examples.

DETAILED DESCRIPTION OF A PREFERRED EMBODIMENT

Figure 1:
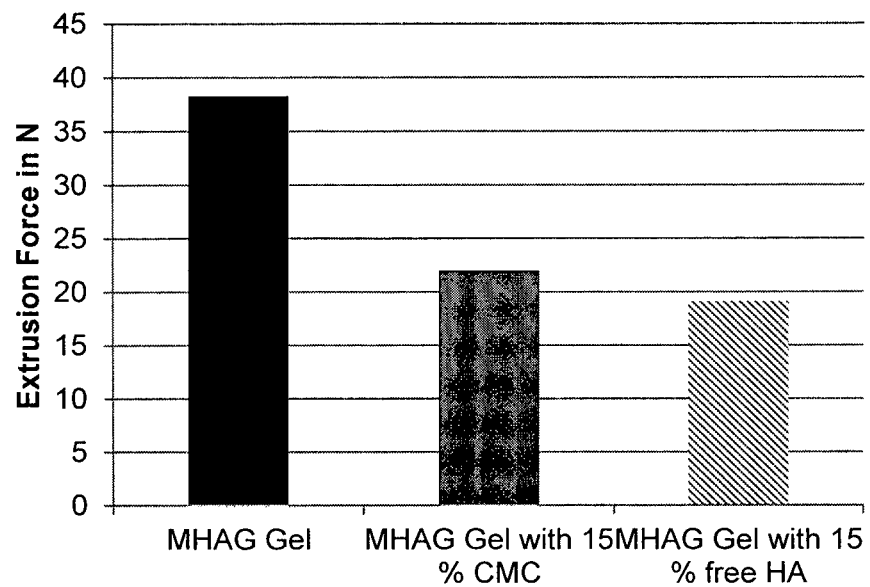
FIGS. 1-7 depict embodiments as described herein.

FIG. 1 shows the extrusion force of a HA/CMC dermal filler composition according to the present invention (MHAG gel with 15% (v/v) CMC; gray bar) and a HA/free HA dermal filler composition (MHAG gel with 15% (v/v) free HA; hatched bar) in comparison to a "HA only" gel (MHAG gel; black bar).

Figure 2:
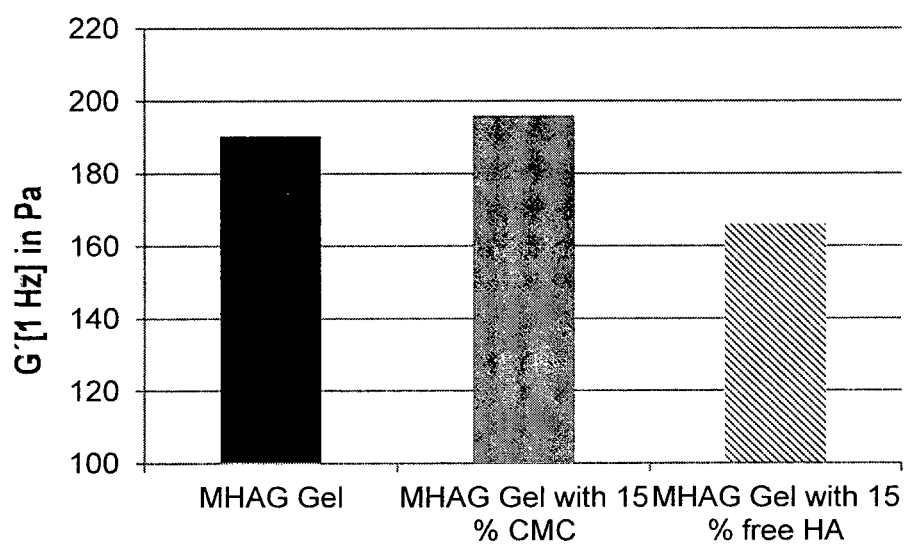

FIG. 2 shows the modulus of elasticity (G') of a HA/CMC dermal filler composition according to the present invention (MHAG gel with 15% (v/v) CMC; gray bar) and a HA/free HA dermal filler composition (MHAG gel with 15% (v/v) free HA; hatched bar) in comparison to a "HA only" gel (MHAG gel; black bar).

Figure 3:
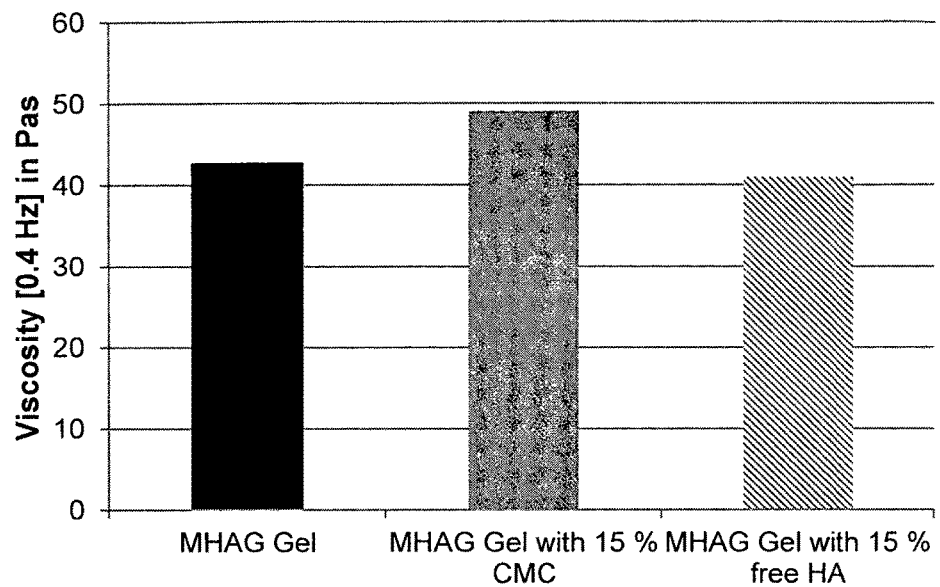

FIG. 3 shows the viscosity of a HA/CMC dermal filler composition according to the present invention (MHAG gel with 15% (v/v) CMC; gray bar) and a HA/free HA dermal filler composition (MHAG gel with 15% (v/v) free HA; hatched bar) in comparison to a "HA only" gel (MHAG gel; black bar).

Figure 4:
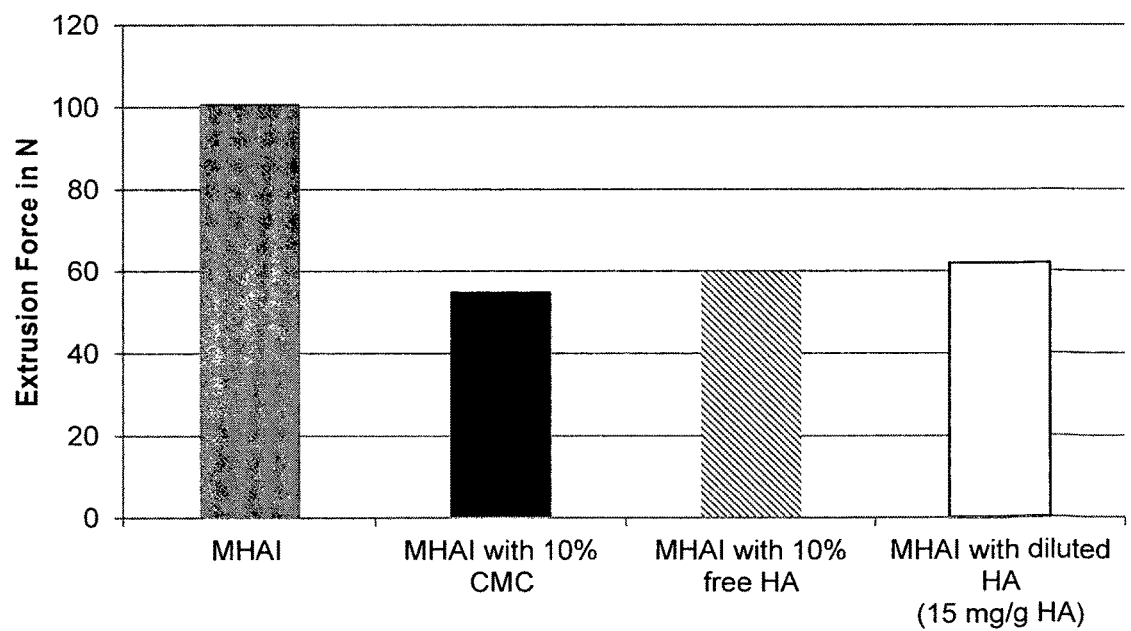

FIG. 4 shows the extrusion force of a HA/CaHAP/CMC dermal filler composition according to the present invention (MHAI with 10% (v/v) CMC; black bar) in comparison a HA/CaHAP gel (MHAI; gray bar), a HA/CaHAP/free HA gel (MHAI with 10% free HA; hatched bar), and a dilution of the MHAI gel (MHAI with diluted HA (15 mg/ml HA); open bar).

Figure 5:
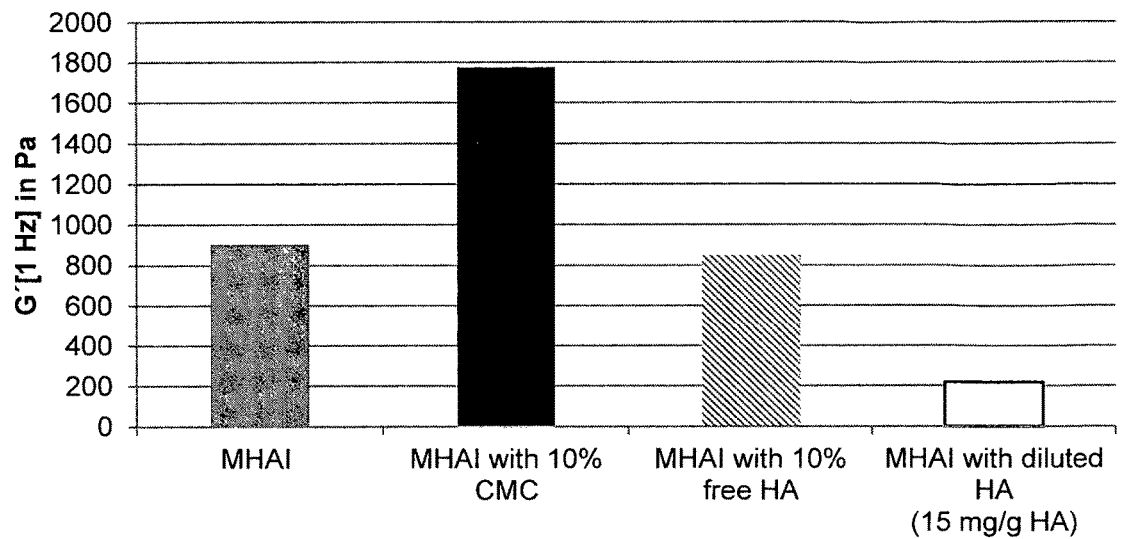

FIG. 5 shows the modulus of elasticity (G') of a HA/CaHAP/CMC dermal filler composition according to the present invention (MHAI with 10% (v/v) CMC; black bar) in comparison to a HA/CaHAP gel (MHAI; gray bar), a HA/CaHAP/free HA gel (MHAI with 10% free HA; hatched bar), and a dilution of the MHAI gel (MHAI with diluted HA (15 mg/ml HA); open bar).

Figure 6:
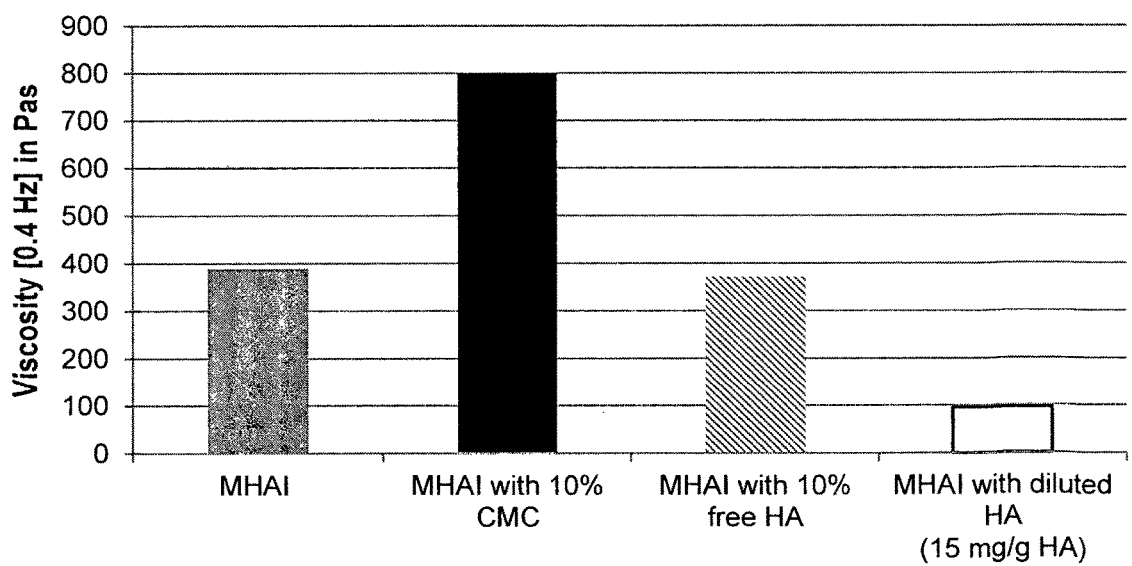

FIG. 6 shows the viscosity of a HA/CaHAP/CMC dermal filler composition according to the present invention (MHAI with 10% (v/v) CMC; black bar) in comparison to a HA/CaHAP gel (MHAI; gray bar), a HA/CaHAP/free HA gel (MHAI with 10% free HA; hatched bar), and a dilution of the MHAI gel (MHAI with diluted HA (15 mg/ml HA); open bar).

Figure 7:
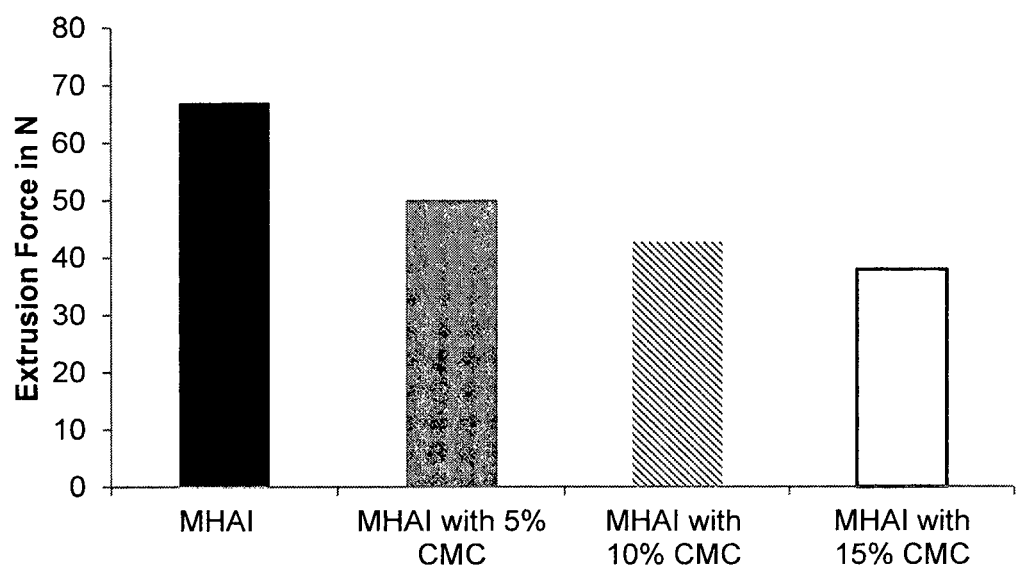

FIG. 7 shows the influence of different concentrations of CMC on the extrusion force of a HA/CaHAP dermal filler (MHAI; black bar), a HA/CaHAP gel with 5% CMC (MHAI with 5% CMC; gray bar), a HA/CaHAP gel with 10% CMC (MHAI with 10% CMC; hatched bar) and a HA/CaHAP gel with 15% CMC (MHAI with 15% CMC; open bar).

DETAILED DESCRIPTION OF THE INVENTION

The injectable dermal filler of the present invention provides a number of advantages over known fillers, including excellent biocompatibility, improved persistence, high moisture retention, no immunogenicity, and safe absorption by the body, while maintain desirable mechanical and rheological properties for use as a dermal filler.

In particular, the inventors of the present invention have found that the addition of a small quantity of carboxymethyl cellulose (CMC) to a crosslinked HA gel surprisingly leads to a long-lasting dermal filler composition displaying a low extrusion force, while having improved mechanical properties (i.e. high modulus of elasticity (G') and high dynamic viscosity) providing high volumizing capacity. In other words, the dermal filler according to the present invention was unexpectedly found to provide an optimal balance of longevity, lifting capacity and ease of injection.

Furthermore, in a preferred embodiment of the present invention, where the dermal filler composition additionally contains microparticles (e.g., calcium hydroxyapatite (CaHAP) microparticles), the advantages of Radiesse (i.e. neocollagenesis due to calcium hydroxyapatite particles) are combinable with the advantage of a partial reversibility/correctability due to the possibility of using a hyaluronidase enzyme to degrade and dissolve the crosslinked HA carrier. Another advantage is that the crosslinked HA carrier will last longer than the current uncrosslinked CMC carrier used, e.g., in Radiesse®. This will prevent the known gap of performance/volumizing effect, which is seen between the time of dissolution of CMC and the induction of neocollagenesis by the microparticles.

In a first aspect, the present invention relates to an injectable dermal filler composition in the form of a gel, comprising crosslinked hyaluronic acid and carboxymethyl cellulose.

As used herein, the term "dermal filler" broadly refers to a material or composition designed to add volume to areas of soft tissue deficiency. The term "dermal filler", as used herein, has the same meaning as, and is interchangeably used with, the term "soft tissue filler". This is, the term "dermal filler" should not be construed as imposing any limitations as to the location and type of injection, and it generally encompasses uses at multiple levels beneath the dermis, for example sub-muscularly above the periosteum and in the subcutaneous plane. Within the meaning of the present invention, the term "soft tissue" generally relates to tissues that connect, support, or surround other structures and organs of the body. In the present invention, soft tissues include, for example, muscles, tendons (bands of fiber that connect muscles to bones), fibrous tissues, fat, blood vessels, nerves, and synovial tissues (tissues around joints).

According to the present invention, the injectable dermal filler composition is a gel. The term "gel", as used herein, generally refers to a material having fluidity at room temperature between that of a liquid and solid. In addition, the term "gel" is intended to mean a material capable of absorbing water (i.e. a "hydrogel"). Within the present invention, the injectable dermal filler composition generally comprises a physiologically acceptable carrier fluid, such as an apyrogenic isotonic buffer, in particular a physiological saline solution that is preferably buffered.

Furthermore, the dermal filler composition of the present invention is "injectable". This means that the dermal filler composition is suitable for injection into the skin or other tissue in order to bring the dermal filler composition to the desired target site. An "injectable" composition within the meaning of the present invention can be dispensed from syringes under normal conditions under normal pressure.

In accordance with the present invention, the concentration of the carboxymethyl cellulose is preferably between 1.0% to 25.0%, more preferably between 5.0% to 20%, and most preferably between 10% and 15% volume/volume. Within the present invention, it is generally used as a lubricant or lubrication phase. A suitable carboxymethyl cellulose for use herein may have a molecular weight in the range of $5.0 \times 10^4$ Da (low viscosity CMC) to $1.5 \times 10^6$ Da (high viscosity CMC), for example in the range of $9.0 \times 10^4$ Da to $7.0 \times 10^5$ Da, in particular in the range of $1.5 \times 10^5$ to $5.0 \times 10^5$ Da.

Furthermore, a suitable carboxymethyl cellulose for use herein may be selected from a low viscosity carboxymethyl cellulose having a viscosity of 75 mPa·s to 750 mPa·s, as measured with a Brookfield spindle viscosimeter (model LVT) at 25° C. and a rotary speed of 60 rpm with spindles of size No. 1 or No. 2 using a 2% aqueous solution, a medium viscosity carboxymethyl cellulose having a viscosity of 750 mPa·s to 4,000 mPa·s, as measured with a Brookfield spindle viscosimeter (model LVT) at 25° C. and a rotary speed of 30 rpm with spindles of size No. 2 or No. 3 using a 2% aqueous solution, and a high viscosity carboxymethyl cellulose having a viscosity of 4,000 mPa·s to 25,000 mPa·s, as measured with a Brookfield spindle viscosimeter (model LVT) at 25° C. and a rotary speed of 30 rpm with spindles of size No. 3 or 4 using a 1% aqueous solution.

Moreover, the carboxymethyl cellulose has typically a degree of substitution of 0.20 to 1.50, preferably 0.40 to 1.10, more preferably 0.60 to 0.95, and most preferably 0.70 to 0.90. As used herein, the "degree of substitution" (degree of etherification), as used herein, is defined as follows: $[C_6H_7O_2(OH)_x(OCH_2COO_m)_y]_n$, where n is the degree of polymerization (e.g., 450 to 4.000) and x+y=3, wherein y is the degree of substitution. The degree of substitution can be determined as known in the art (e.g., according to the method described in the International Oenological Codex COEI-1-CMC:2009).

The hyaluronic acid is present in the composition in a concentration of preferably 0.1% to 5.0% or 0.2% to 4.5% or 0.3% to 4.0% or 0.4% to 4.0% or 0.5% to 4.0% or 0.7% to 4.0% or 1.0% to 4.0%, more preferably 0.5% to 3.0% or 1.0% to 3.0% or 1.5% to 3.0% or 2.0% to 3.0%, most preferably 1.0% to 2.5% or 2.0% to 2.5% weight/volume. Within the present invention, the crosslinked HA forms a "matrix". As used herein, the term "matrix" is intended to mean a network of polysaccharides, either crosslinked or non-crosslinked, in the form of a solution or gel. Furthermore, the term "hyaluronic acid" or "HA", as used herein, means hyaluronic acid, hyaluronate, and any hyaluronate salt such as sodium hyaluronate.

In the context of the present invention, the crosslinked hyaluronic acid is not limited in any way and includes crosslinked hyaluronic acid prepared from a single hyaluronic acid or from two or more hyaluronic acids that differ in their molecular weight (see, e.g., US 2010/0316683 A1 or WO 2013/185934 A1, which are incorporated herein by reference). Also, within the scope of the present invention, the crosslinked hyaluronic acid may form a "polydensified" gel which is characterized by a variation of the degree of crosslinking within the gel, i.e. a "polydensified" gel has (at least) two different density levels with denser parts (higher degree of crosslinking) and less dens parts (lower degree of crosslinking).

Polydensified gels can be prepared, for example, by a first crosslinking reaction to crosslink first polysaccharide(s), followed by a second crosslinking reaction to crosslink second polysaccharide(s) to form a double-crosslinked gel. Said first and said second polysaccharide(s) may, for example, independently be the same hyaluronic acid or two different hyaluronic acids which differ in their mean molecular weight (e.g., a low molecular weight and a high molecular weight hyaluronic acid). The double-crosslinking process (dynamic cross-linking technology) is known in the art and is described, for example, in EP 1 711 552 B1, which is incorporated herein by reference.

Within the present invention, the crosslinked hyaluronic acid may be prepared by crosslinking a single hyaluronic acid or by crosslinking a first hyaluronic acid and a second hyaluronic acid, and, optionally, at least one further hyaluronic acid, wherein the first, second and at least one further hyaluronic acid differ in their mean molecular weights.

Preferably, said single hyaluronic acid has a mean molecular weight of $0.1 \times 10^6$ to $4.0 \times 10^6$ Da or $0.3 \times 10^6$ to $4.0 \times 10^6$ Da or $0.5 \times 10^6$ to $4.0 \times 10^6$ Da, in particular $1.0 \times 10^6$ to $3.0 \times 10^6$ Da or $1.5 \times 10^6$ to $2.5 \times 10^6$ Da. Said first hyaluronic acid has preferably a mean molecular weight of $1.0 \times 10^5$ Da to less than $1.0 \times 10^6$ Da, more preferably $3.0 \times 10^5$ Da to $9.0 \times 10^5$ Da, and most preferably $5.0 \times 10^5$ Da to $8.0 \times 10^5$ Da. Said second hyaluronic acid has usually a mean molecular weight of greater than $1.0 \times 10^6$ Da up to $5.0 \times 10^6$ Da, in particular between $1.5 \times 10^6$ Da and $4.0 \times 10^6$ Da, and preferably between $2.0 \times 10^6$ Da and $3.0 \times 10^6$ Da. The weight ratio of the first HA to the second HA in the injectable dermal filler composition of the present invention is not limited and may, for example, range from 0.001:99.999 to 99.999:0.001, preferably from about 70:30 to about 99.9:0.1, and most preferably from about 90:10 to about 99.0:1.0.

Various methods can be applied herein to determine the molecular weight of HA, such as intrinsic viscosity measurements (e.g., according to Chinese Pharmacopoeia, $2^{nd}$ revision, 2006), capillary electrophoresis (CE) (e.g., according to Kinoshita et al., Biomed. Chromatogr., 2002, 16:141-45), high performance gel permeation chromatography (HPGPC) (e.g., according to Kim et al., Food Chem., 2008, 109: 63-770), and multi-angle laser light scattering combined with size-exclusion chromatography (SEC-MALLS) (e.g., in accordance to Hokputsa et al., Eur. Biophys. J. Biophys. Lett., 2003, 32:450-456).

Preferably, the injectable dermal filler composition according to the present invention is crosslinked with BDDE (1,4-butanediol diglycidyl ether). The BDDE-crosslinked hyaluronic acid may have a degree of modification, expressed as the ratio of the sum of mono- and double-linked BDDE-crosslinkers to the sum of hyaluronic acid disaccharide units, of 0.5% to 25%, preferably 1.0% to 15%, more preferably 2.0% to 10%, and most preferably 3.0% to 8.0% or 4.0% to 7%.

The degree of modification can be determined by NMR in accordance with methods known in the art (Edsman et al., Gel Properties of Hyaluronic Acid Dermal Fillers, Dermatol. Surg. 2012, 38:1170-1179; Guarise et al., SEC determination of cross-link efficiency in hyaluronan fillers, Carbohydrate Polymers 2012, 88:428-434; Kenne et al., Modification and cross-linking parameters in hyaluronic acid hydrogels—Definitions and analytical methods, Carbohydrate Polymers 2013, 91:410-418).

In brief, the dialyzed and sterilized gels are degraded before conducting the NMR measurement. The degradation can be performed by chondroitinase AC (Edsman et al., supra; Kenne et al., supra), NaOH (Guarise et al., supra), addition of hyaluronidase (e.g., 150 U ovine hyaluronidase to 1 g of gel) or by incubation at 90° C. for at least 35 h. The obtained solutions are then lyophilized, dissolved in $D_2O$, and well homogenized.

The NMR measurement can be performed at, e.g., 500 MHz, at a pulse of 20 degree with several repetitions at ambient temperature to receive a spectrum with appropriate resolution. In accordance with the literature, the degree of modification (MoD) is assessed by calculating the ratio of the N-acetyl signals of HA to the methylene signals of BDDE. For N-acetyl of HA, the critical signals are located at about 2.0 ppm and at about 1.6 ppm for BDDE when solubilized in $D_2O$. In order to calculate the degree of modification, the integral values were identified and the ratio of protons of 3H of N-acetyl ($CH_3$) to 4H of methylene ($CH_2CH_2$) needs to be taken in account, in accordance with the literature (Edsman et al., supra, and Kenne et al., supra).

According to a preferred embodiment of the present invention, the injectable dermal filler composition further comprises resorbable biocompatible microparticles. The term "microparticles", as used herein generally relates to substantially rounded or spherical particles. In addition, the microparticles preferably have a mean diameter of 5 µm to 500 µm, more preferably 10 µm to 200 µm, particularly preferably 15 µm to 100 µm or 20 µm to 75 µm, and most preferably 25 µm to 45 µm. Within the context of the present invention, the term "resorbable" generally refers to a material that can be broken down and absorbed into a tissue and/or body fluid.

The microparticles are preferably present in the composition in a concentration of 0.5% to 50% or 1.0% to 50%, more preferably 1.0% to 40%, particularly preferable 5.0% to 35%, in particular 15.0% to 30% or 20% to 25%, and most preferable 25.0% to 35% volume/volume.

Within the context of the present invention, the resorbable biocompatible microparticles may consist of calcium phosphate-based materials, alumina-based materials, a biodegradable natural polysaccharide or a derivate thereof, or a biodegradable polyester, polyorthoester or polyanhydride synthetic polymer.

The term "natural polysaccharide", as used herein, generally relates to a polysaccharide that occurs in nature. As used herein, a "derivative", when used in connection with a natural polysaccharide, refers to a polysaccharide that is derived from the natural polysaccharide by chemical modification such as carboxylation, etherification, methylation, sulfonation, and the like. The term "biodegradable", as used herein, broadly refers to materials that are capable of being decomposed in vivo by living humans and should not be construed to be restricted to a particular decomposition time or duration.

The calcium phosphate-based materials may be selected from calcium hydroxyapatite, calcium fluoroapatite, calcium chloroapatite, calcium carbonate apatite, tetracalcium phosphate, calcium pyrophosphate, tricalcium phosphate, and octacalcium phosphate. Preferably, the calcium phosphate-based material is calcium hydroxyapatite.

The biodegradable polyester, polyorthoester or polyanhydride synthetic polymer may be a homopolymer or copolymer of glycolide, lactide, caprolactone, and p-dioxanone, or is trimethylene carbonate, or a poly(hydroxybutyrate) or poly(hydroxyvalerate) polymer. Preferably, the biodegradable polyester, polyorthoester or polyanhydride synthetic polymer is selected from poly-ε-caprolactone, polyglycolides, polylactides, polydioxanone, poly(lactic-co-glycolic acid), poly(glycolide-co-caprolactone), and poly (glycolide-co-trimethylene carbonate), and is most preferred poly-ε-caprolactone or polydioxanone.

In accordance with the present invention, the injectable dermal filler composition may further comprising one or more compounds selected from the group consisting of polyols, vitamins, amino acids, metals, antioxidants, and mineral salts. Suitable polyols for use herein include, but are not limited to, glycerin, mannitol, sorbitol, propylene glycol, erythritol, xylitol, maltitol, and lactitol. Particularly suitable for use herein is mannitol and glycerin. Further, the polyol is preferably glycol, optionally in combination with one or more of the aforementioned polyol compounds, in particular mannitol. The poyol(s) may, for example, be included in the injectable dermal filler composition in a concentration of 1% to 25% or 2% to 17% or 3% to 13% volume/volume, in particular in a concentration of 5% to 11% or 7% to 10% volume/volume.

Suitable vitamins include vitamin C, vitamin E and vitamins of the B group, i.e. one or more of $B_1$, $B_2$, $B_3$, $B_5$, $B_6$, $B_7$, $B_9$ and $B_{12}$ vitamins. The concentration of vitamin C or of vitamin E is preferably from about 0.01 mg/ml to about 10.0 mg/ml, more preferably from about 0.1 mg/ml to about 5.0 mg/ml, and the total concentration of the vitamins of the B group is preferably from about 0.01 mg/ml to about 10.0 mg/ml, more preferably from about 0.1 mg/ml to about 5.0 mg/ml. The vitamins may be present to stimulate and maintain cellular metabolism and, thus, to promote collagen production. Particularly preferred for use here is vitamin C, vitamin E and vitamin. $B_6$.

Furthermore, the injectable dermal filler composition according to the present invention may further comprises an anesthetic, in particular a local anesthetic, preferably lidocaine, in a concentration of, for example, 0.05 wt. % to 5.0 wt. %, 0.1 wt. % to 4.0 wt. %, 0.2 wt. % to 3.0 wt. %, 0.3 wt. % to 2.0 wt. %, or 0.4 wt. % to 1.0 wt. %.

It is further contemplated herein that the injectable dermal filler composition may include crosslinked and/or non-crosslinked polymers other than the crosslinked HA and CMC. In particular, the injectable dermal filler composition may further comprise 0.001% to 15%, in particular 1% to 10% volume/volume non-crosslinked hyaluronic acid. The molecular weight of said non-crosslinked hyaluronic acid is preferably between $3.0 \times 10^5$ Da and $4.0 \times 10^6$ Da, in particular between $1.0 \times 10^6$ Da and $3.0 \times 10^6$ Da.

Other crosslinked or non-crosslinked polymers, such as chondroitin sulfate, keratan, keratan sulfate, heparin, heparin sulfate, cellulose and its derivatives, chitosan, carrageenan, xanthan, and alginate, or one of their salts, may also be included in the injectable dermal filler composition of the present invention in low amounts (e.g., less than 10%, usually less than 5% or less than 1% volume/volume). However, it is also contemplated herein that the injectable dermal filler composition lacks any crosslinked polymers other than the crosslinked HA described herein and/or lacks any non-crosslinked polymers other than the CMC described herein. In this context, the term "polymer", as used herein, refers to any natural or synthetic polymeric compound with repeating structural units, including polysaccharides such as HA.

In a preferred embodiment of the present invention, the injectable dermal filler composition according to the present invention, including the composition that comprises microparticles (e.g., calcium hydroxyapatite microparticles), further comprises an anesthetic, preferably lidocaine, and/or one or more polyols described above. Particularly preferred, the injectable dermal filler composition according to the present invention, including the composition that comprises CaHAP microparticles, further comprises lidocaine and glycerin.

Moreover, in accordance with the present invention, the injectable dermal filler composition may have one or more of the following properties:
(i) an elastic modulus G' at a frequency (f) of 0.4 Hz and 25° C. of 50 Pa to 4.500 Pa, preferably 100 Pa to 4000 Pa, more preferably 150 Pa to 2,500 Pa;
(ii) a viscosity at a frequency of 0.4 Hz and 25° C. of 20 Pa·s to 1,400 Pa·s, preferably of 25 Pa·s to 1,000 Pa·s, more preferably 30 Pa·s to 900 Pa·s; and
(iii) a tan delta (G"/G') at a frequency of 0.4 Hz and 25° C. of 0.20 to 0.8, preferably 0.25 to 0.6.

In addition, the extrusion force for an injectable dermal filler composition according to the present invention that lacks any microparticles (e.g., calcium hydroxyapatite microparticles) is generally in the range of 10 N to 30 N, as measured through a (e.g., Neoject) 25 G×⅝" needle at an extrusion rate of about 50 mm/min using a standard 1 ml syringe (e.g., a 1.0 ml BD syringe). The extrusion force for an injectable dermal filler composition according to the present invention with microparticles (e.g., calcium hydroxyapatite microparticles) is generally in the range of 35 N to 70 N, as measured through a (e.g., Terumo K pack II) 25 G TW ¾ needle at an extrusion rate of about 50 mm/min using a standard 1.5 ml syringe (e.g., a 1.5 ml plastic syringe).

Furthermore, the injectable dermal filler composition usually comprises a buffer, for example a phosphate buffer, to adjust the pH. Since the injectable dermal filler composition of the present invention is intended for insertion into the human body, the pH is generally in the range of 6.5 to 7.5, preferably in the range of 6.8 to 7.4. In addition, the osmolality is preferably about 200 mOsmol/l to about 400 mOsmol/l, more preferably about 280 mOsmol/l to about 330 mOsmol/l.

In a second aspect, the present invention relates to kit comprising the injectable dermal filler composition according to the first aspect of the present invention. The kit may also comprise instructions for use.

In a third aspect, the present invention relates to method for preparing an injectable dermal filler composition according to the first aspect of the present invention, comprising the following steps:
(a) providing a crosslinked hyaluronic acid gel,
(b) providing a carboxymethyl cellulose gel,
(c) mixing the crosslinked hyaluronic acid gel and the carboxymethyl cellulose gel.

The crosslinked hyaluronic acid gel provided in step (a) and/or the carboxymethyl cellulose gel provided in step (b) preferably comprises one or more of the polyols mentioned above, in particular glycerin. Additionally or alternatively, one or more of the polyols mentioned above, in particular glycerin, may also be added in step (c) or after step (c). Furthermore, within the present invention, the microparticles may be suspended in the carboxymethyl cellulose gel provided in step (b) or, alternatively, the microparticles may be mixed together with the crosslinked hyaluronic acid gel and the carboxymethyl cellulose gel in step (c). Also, the microparticles may be added to the mixture obtained in step (c).

Preferably, the crosslinked hyaluronic gel of step (a) and/or the carboxymethyl cellulose gel of step (b) comprises an anesthetic, e.g. lidocaine. More preferably, the anesthetic (e.g., lidocaine) is added in step (c) or, after step (c), to the mixture obtained in step (c).

In a fourth aspect, the present invention relates to the use of an injectable dermal filler composition according to the first aspect of the present invention or a kit according to the second aspect of the present invention for cosmetic applications.

The use according to the fourth aspect preferably includes the cosmetic treatment of wrinkles and lines of the skin (e.g., facial lines and facial wrinkles), glabellar lines, nasolabial folds, chin folds, marionette lines, buccal commissures, peri-oral wrinkles, crow's feet, cutaneous depressions, scars, temples, subdermal support of the brows, malar and buccal fat pads, tear troughs, nose, lips, cheeks, perioral region, infraorbital region, facial asymmetries, jawlines, and chin.

In a fifth aspect, the present invention relates to an injectable dermal filler composition according to the first aspect of the present invention for use in therapy. In particular, the injectable dermal filler composition according to the first aspect of the present invention may be used in treating stress urinary incontinence, vesico-ureteral reflux, vocal fold insufficiency, vocal fold medialization.

In a sixth aspect, the present invention relates to a method for replacing or filling of a biological tissue or increasing the volume of the biological tissue, comprising administering to a subject in need thereof an effective amount of the injectable dermal filler composition according the first aspect of the present invention.

Typically, the injectable dermal filler composition is administered by injection such as by subcutaneous or intradermal injection. For example, the composition may be intradermally or subcutaneously injected using the serial puncture technique. The term "effective amount" refers to the amount of the injectable dermal filler composition sufficient to effect beneficial or desired cosmetic (aesthetic) or therapeutic results. A "subject" in the sense of the present invention is any individual or patient in need of the treatment of a particular condition or disease. Within the framework of the present invention, the subject is usually a human.

The composition is preferably administered for treating a cosmetic condition, such as the treatment of wrinkles or lines of the skin (e.g., facial lines and facial wrinkles), glabellar lines, nasolabial folds, chin folds, marionette lines, buccal commissures, perioral wrinkles, crow's feet, cutaneous depressions, scars, temples, subdermal support of the brows, malar and buccal fat pads, tear troughs, nose, lips, cheeks, perioral region, infraorbital region, facial asymmetries, jawlines, and chin. However, the composition may also be administered for treating a therapeutic indication such as stress urinary incontinence, vesico-ureteral reflux, vocal fold insufficiency, vocal fold medialization.

All the explanations and comments provided above in relation to the first aspect of the invention (e.g., with regard to ingredients or substances comprised in the injectable dermal filler composition, its manufacturing method, and the definitions of some technical terms) equally apply to the method according to the sixth aspect of the invention.

The present invention will now be further illustrated by the following, non-limiting examples.

EXAMPLES

The examples provided below demonstrate that the dermal filler composition according to the present invention has a significantly reduced extrusion force, while its mechanical properties (i.e. modulus of elasticity (G') and viscosity) are unexpectedly maintained or even improved.

Measurement of Extrusion Force

Extrusion force of HA gels (with or without CMC or free HA lubrication phase) was determined with 1.0 ml BD syringe and Neoject 25 G×⅝" needles. For this purpose, a Texture analyzer TA.XTPLUS was used. Testing was performed using a preload of 0.500 N, and a testing speed of 2 in/min.

Extrusion force of HA/CaHAP gels (with or without CMC or free HA lubrication phase) was determined with 1.5 ml plastic syringe and Terumo K pack II 27 G TW ¾ needles. For this purpose, a Texture analyzer TA.XTPLUS was used. Testing was performed using a preload of 0.500 N, and a testing speed of 2 in/min.

Measurement of the Modulus of Elasticity (G') and Dynamic Viscosity

The modulus of elasticity (G') and viscosity was measured using an Anton Paar MCR 302 rheometer equipped with a plate-plate system with a diameter of 20 mm.

In the case of HA gels (with or without CMC or free HA lubrication phase), the G' and viscosity were determined using the following settings:

| | |
|---|---|
| Temperature | 30° C. |
| Gap Size | 1.0 mm |
| Plate Size | PP35 |
| Tau (Stress) | 5 Pa |
| Frequency Range | 0.1-10 Hz |
| Frequency/Decade | 6 |

In the case of HA/CaHAP gels (with or without CMC or free HA lubrication phase), the G' and viscosity were determined using the following settings:

| | |
|---|---|
| Temperature | 25° C. |
| Gap Size | 2 mm |
| Plate Size | PP20 |
| Tau (Stress) | 30 Pa |
| Frequency Range | 0.1-10 Hz |
| Frequency/Decade | 6 |

Example 1

Preparation of HA Gels without Lubrication Phase and with or without Calcium Hydroxyapatite (CaHAP) Particles (MHAG Gel and MHAI Gel) (Comparative Gels)

Preparation of Crosslinking Solutions

A HA "cake" was prepared by dissolving 43 g sodium hyaluronate (mean molecular weight of about 2.8 MDa) in 270.35 g of phosphate buffer. The obtained HA cake can be stored in a refrigerator until needed. Further, an alkaline solution was prepared by dissolving 3.31 g of solid sodium hydroxide in 10 ml of buffer. In addition, a BDDE solution was prepared by mixing 12.5 g of 2M NaOH solution with 88.5 g of phosphate buffer and then by mixing 8.21 ml of this solution and 3.395 ml of BDDE.

Crosslinking

The HA cake was manually broken into small pieces, The alkaline solution in its entirety was added to a bowl, followed by mixing for 30 to 40 minutes at 12 rpm. Then, the BDDE solution was added into the bowl and mixing was continued for 10 to 15 minutes at 25 rpm. The temperature set point was changed to 33.33° C. and the mixture was let for 4 hours at this temperature.

Neutralization and Purification

A neutralization solution was prepared by adding 920.99 g of buffer to 84.62 g 1 M HCl. The whole neutralization solution was then added into the bowl and stirred for 2 hours at 5° C. Afterwards, the gel was purified according to methods known to those skilled in the art. The resulting gel (the "MHA gel") was then used to prepare the MHAG (without CaHAP) and the MHAI (with CaHAP) gel formulations described below.

MHAG Gel

In order to prepare the MHAG gel, a concentrated lidocaine solution "LS1" was prepared by adding 2 g of lidocaine to 2 g of phosphate buffer, followed by gentle stirring using a magnetic stirrer until complete dissolution. Then, 467 g of the MHA gel prepared in Example 1 was mixed with 2116 µl of "LS1" solution for 15 minutes using an appropriate mixer. Afterwards, 33 g of glycerin was added and the compounds were mixed moderately for 1.5 hours. After a further degassing step, 1 ml syringes were filled and sterilized at 127° C. for 4 min.

MHAI Gel

In addition, a gel that corresponds to the MHAG gel but additionally contains CaHAP particles in the same amount as the gels prepared in Examples 4 to 6 was prepared in accordance with the procedure described above for the MHAG gel. This crosslinked HA gel with CaHAP is designated "MHAI" hereinbelow.

Example 2

Preparation of a HA Gel with 15% CMC as Lubrication Phase (Inventive Gel)

A solution "LB1" was prepared by adding 62.75 g of glycerin to 2.150 g of lidocaine HCl and dissolving this mixture in 135.142 g of phosphate buffer. A gentle stirring using a magnetic stirrer was then performed until complete dissolution.

Next, 2.764 g of NaCMC is mixed strongly for 1 hour in a bowl with 105.24 g of LB1. After degassing, 392.025 g of the MHAG gel prepared in Example 1 were added and mixed moderately for 1.5 hours. After a further degassing step, 1 ml syringes were filled and sterilized at 127° C. for 4 min.

Example 3

Preparation of a HA Gel with 15% (v/v) Free HA as Lubrication Phase (Comparative Gel)

A solution "LB2" was prepared by dissolving 1.131 g of lidocaine HCl in 72.743 g of phosphate buffer. Then, 1.170 g of sodium hyaluronate (2.5-3.0 MDa) were added. After complete dissolution, 33.005 g of glycerin were added. The mixture was then stirred at a moderate speed for 1 hour and 30 minutes and kept at 5° C. before use.

A HA gel with 15% (v/v) free HA lubricant was prepared by mixing 106.721 g of LB2 with 387.357 g of the MHAG gel prepared in Example 1. A moderate mixing was maintained for 2 hours. After degassing, the mixture was transferred in 1 ml syringes and sterilized at 127° C. for 4 min.

Example 4

Preparation of a HA/CaHAP Gel with 5% (v/v) CMC as Lubrication Phase (Inventive Gel)

A solution "LB3" was prepared in the same manner as for LB1, except that the following materials and quantities were used: 4.633 g of NaCMC, 274.16 g of glycerin, and 121.3 g of phosphate buffer.

A HA/CaHAP gel with 5% (v/v) CMC lubricant was prepared by placing 280.02 g of CaHAP (25 µm to 45 µm), 48.22 g of LB3, and 171.84 g of the MHAG gel prepared in Example 1 in a mixing bowl. Then, 2.120 ml of a lidocaine solution (2 g of lidocaine in 2 g of phosphate buffer) was added. The mixture was stirred at moderate speed for 1.5 hours. After degasing under vacuum, 1 ml syringes were filled and sterilized at 121° C. for 20 minutes.

Example 5

Preparation of a HA/CaHAP Gel with 10% (v/v) CMC as Lubrication Phase (Inventive Gel)

A solution "LB4" was prepared in the same manner as for LB1, except that the following materials and quantities were used: 7.039 g of NaCMC, 208.527 g of glycerin, and 184.46 g of phosphate buffer.

A HA/CaHAP gel with 10% (v/v) CMC lubrication was prepared as described in Example 4, except that the following quantities were used: 280.02 g of CaHAP (25 µm to 45 µm), 63.29 g of LB4, and 156.79 g of the MHAG gel prepared in Example 1.

Example 6

Preparation of a HA/CaHAP Gel with 15% (v/v) CMC as Lubrication Phase (Inventive Gel)

A solution "LB5" was prepared in the same manner as for LB1, except that the following materials and quantities were used: 8.529 g of NaCMC, 168.266 g of glycerin, and 223.29 g of phosphate buffer.

A HA/CaHAP gel with 15% (v/v) CMC lubricant was prepared as described in Example 4, except that the following quantities were used: 280.02 g of CaHAP (25 µm to 45 µm), 78.46 g of LB5, and 141.562 g of the gel MHAG prepared in Example 1.

Example 7

Preparation of a HA/CaHAP Gel with 10% (v/v) Free HA as Lubrication Phase (Comparative Gel)

A solution "LB6" was prepared in the same manner as for LB2, except that the following materials and quantities were used: 208.548 g of glycerin, 3.108 g of sodium hyaluronate, and 188.581 g of phosphate buffer.

A HA/CaHAP gel with 10% (v/v) free HA lubricant was prepared by mixing 156.781 g of the MHAG gel prepared in Example 1 with 63.32 g of LB6 and 2120 µL of lidocaine solution (2 g of lidocaine in 2 g of phosphate buffer). Then, 280.02 g of CaHAP (25 µm to 45 µm) were added and mixed moderately for 1.5 hours. After degassing, 1 ml syringes were filled and sterilized at 121° C. for 20 min.

Example 8

Effect of CMC Lubricant or Free HA Lubricant on the Extrusion Force of a Crosslinked HA Gel In this example, the effect of adding CMC or free HA as lubricant on the extrusion force of a HA gel was examined. To this end, the extrusion force of the following gels was measured: MHAG gel (Example 1), MHAG with 15% CMC (Example 2) and MHAG gel with 15% free HA (Example 3).

It was found that the use of CMC as a lubricant significantly decreased the extrusion force. The decrease was similar to that observed with free HA (see FIG. 1).

Example 9

Impact of CMC Lubricant or Free HA Lubricant on the Modulus of Elasticity (G) of a Crosslinked HA Gel In this example, the impact of CMC lubricant and free HA lubricant on the modulus of elasticity (G') of a HA gel was examined. To this end, the G' (at 1 Hz, 25° C.) of the same gels as in Example 8 was measured.

It was found that the addition of CMC slightly increased G', while the addition of free HA decreased G' (see FIG. 2). Preservation of G' is important since this parameter influences the lifting capacity of a filler. Thus, as there was even a slight increase observed with CMC, the MHAG gel with 15% (v/v) CMC is expected to be less likely displaced once under the skin, thereby resulting in more "lift".

Example 10

Influence of CMC Lubricant or Free HA Lubricant on the Viscosity of a Crosslinked HA Gel In this example, the influence of CMC lubricant and free HA lubricant on the viscosity was examined. To this end, the viscosity (at 0.4 Hz, 25° C.) was determined for the same gels as in Example 8.

It was found that the addition of CMC increases the viscosity, while the addition of free HA slightly decreased the viscosity (see FIG. 3). The viscosity is also an important parameter of a filler composition since an increased viscosity will limit the spreading of the gel in the soft tissue and will also contribute to the volumizing effect.

Example 11

Effect of CMC Lubricant or Free HA Lubricant on the Extrusion Force of a Crosslinked HA/CaHAP Gel In order to study whether the addition of calcium hydroxyapatite (CaHAP) particles change the above results obtained for the addition of CMC or free HA to a crosslinked HA gel, the following gels were prepared: MHAI (comprises crosslinked HA and CaHAP particles; see Example 1), MHAI with 10% CMC (Example 5) and MHAI with 10% free HA (Example 7). In addition, a "diluted MHAI" gel was prepared which corresponds to the MHAI gel except that the diluted MHAI gel has a HA concentration of 15 mg/g. The extrusion force of the above-mentioned gels was then measured.

It was found that the addition of 10% CMC lubricant significantly decreased the extrusion force. The decrease was slightly greater than that observed with free HA. In addition, it should be noted that the use of CMC or free HA lubricant provides a decrease of extrusion force similar to that observed with the "diluted MHAI gel" having a less concentrated HA matrix (see FIG. 4).

Thus, the incorporation of CaHAP particles into a crosslinked HA gel does not change the basic outcomes observed for a crosslinked HA gel without CaHAP particles; however, the decrease in extrusion force was even more pronounced in case of a HA gel with CaHAP particles.

Example 12

Impact of CMC Lubricant or Free HA Lubricant on the Modulus of Elasticity (G) of a Crosslinked HA/CaHAP Gel In this example, the impact of CMC lubricant or free HA lubricant on the modulus of elasticity (G') of a crosslinked HA/CaHAP gel was examined. To this end, G' was determined (at 1 Hz, 25° C.) for the same gels as in Example 11.

It was found that the addition of 10% CMC results in a tremendous increase of G'. In contrast, the addition of 10% free HA is accompanied by a slight decrease of G', and the dilution of the HA matrix leads to a strong drop of the modulus of elasticity which will drastically change the gel's properties and the clinical outcomes (see FIG. 5).

As mentioned above, a gel with high G' will result in a better volumizing effect. Accordingly, this example shows that the addition of a CMC lubricant to a crosslinked HA/CaHAP gel results in a superior lifting capacity.

Example 13

Influence of CMC Lubricant or Free HA Lubricant on the Viscosity of a Crosslinked HA/CaHAP Gel In this example, the influence of CMC lubricant or free HA lubricant on the viscosity of a crosslinked HA/CaHAP gel was examined. To this end, the viscosity was determined (at 0.4 Hz, 25° C.) for the same gels as in Example 11.

It was found that the addition of 10% CMC results in a strong increase of the viscosity, while the addition of HA has only a minimal impact. As expected, dilution of the HA matrix results in viscosity loss of no less than about 75%.

In this respect, it should be pointed out that the concentration of the added CMC lubricant may be adjusted depending on the required extrusion force, as shown in Example 14 below.

Example 14

Influence of Varying CMC Lubricant Concentrations on the Extrusion Force of a Crosslinked HA/CaHAP Gel In this example, the correlation between varying concentrations of added CMC lubricant and the extrusion force was examined. To this end, the extrusion force was measured for the following gels: MHAI (crosslinked HA/CaHAP gel; Example 1), MHAI with 5% CMC (Example 4), MHAI with 10% CMC (Example 5), and MHAI with 15% CMC (Example 6).

It was found that the addition of only 5% CMC leads to a significant reduction of the extrusion force, which can be further reduced by the addition of 10% CMC, and still further by the addition of 15% CMC (see FIG. 7).

Overall, the above Examples 1 to 14 show that dilution of a HA gel leads to a decrease of extrusion force, but is also associated with a strong decrease in the modulus of elasticity (G') and the viscosity which will dramatically impair the clinical outcome of the filler. The experiments further show that, if free HA is added as a lubricant, the extrusion force is lowered but, unfortunately, there is also a slight to moderate decrease of G' and the viscosity.

In contrast, if CMC is used as a lubricant in accordance with the present invention, it was surprisingly found that this not only leads to a strongly reduced extrusion force but also to an increase of G' and the viscosity, especially in the case of a crosslinked HA gel with dispersed particles (CaHAP particles). Both the increase in G' and the increase in viscosity results in an improved lifting effect of the dermal filler composition upon injection. Furthermore, due to the crosslinked nature of the HA gel a long-lasting persistence in the human body will be obtained.

Thus, the experiments presented above provide evidence that the dermal filler composition according to the present invention provides an optimal balance of longevity, lifting capacity and ease of injection.

The invention claimed is:

1. An injectable dermal filler composition in the form of a gel, comprising crosslinked hyaluronic acid and uncrosslinked carboxymethyl cellulose, wherein the crosslinked hyaluronic acid is crosslinked with 1,4-butanediol diglycidyl ether (BDDE), wherein the composition further comprises calcium hydroxyapatite microparticles in a concentration of 20% to 40% volume/volume, and wherein the carboxymethyl cellulose is present at a concentration of 5.0% to 20% volume/volume.

2. The injectable dermal filler composition of claim 1, wherein the crosslinked hyaluronic acid is present at a concentration of 1.0% to 4.0% weight/volume.

3. The injectable dermal filler composition off claim 1, wherein the crosslinked hyaluronic acid is present at a concentration of 2.0% to 3.0% weight/volume.

4. The injectable dermal filler composition of claim 1, wherein the crosslinked hyaluronic acid has a degree of modification, expressed as the ratio of the sum of mono- and double-linked BDDE-crosslinkers to the sum of hyaluronic acid disaccharide units, of 0.5% to 25%.

5. The injectable dermal filler composition of claim 1, wherein the carboxymethyl cellulose is present at a concentration of 5% to 15% volume/volume.

6. The injectable dermal filler composition of claim 1, further comprising one or more compounds selected from the group consisting of anesthetics, polyols, vitamins, amino acids, metals, antioxidants, and mineral salts.

7. The injectable dermal filler composition of claim 1, wherein the composition comprises a polyol and/or an anesthetic.

8. The injectable dermal filler composition according to claim 7, wherein the polyol is glycerin, and the anesthetic is lidocaine, and both are present.

9. The injectable dermal filler composition of claim 1, wherein the composition has the following properties:
(i) an elastic modulus G' at a frequency (f) of 0.4 Hz and 25° C. of 100 Pa to 4000 Pa;

(ii) a viscosity at a frequency of 0.4 Hz and 25° C. of 20 Pa s to 1000 Pa s;

(iii) a tan delta ($G7G^1$) at a frequency of 0.4 Hz and 25° C. of 0.25 to 0.6; and (iv) a pH of 6.5-7.5.

10. A kit comprising the injectable dermal filler composition according to claim 1.

11. A method for preparing an injectable dermal filler composition according to claim 1, comprising:
   (a) providing a crosslinked hyaluronic acid gel, wherein the hyaluronic acid is crosslinked with 1,4-butanediol diglycidyl ether
   (b) providing a carboxymethyl cellulose gel,
   (c) providing calcium hydroxyapatite microparticles and
   (d) mixing the crosslinked hyaluronic acid gel, the calcium hydroxyapatite microparticles and the carboxymethyl cellulose gel, wherein the carboxymethyl cellulose is present in the final composition at a concentration of 5.0% to 20% volume/volume and the calcium hydroxyapatite microparticles are present in the final composition at a concentration of 20% to 40% volume/volume.

12. A method for replacing or filling of a biological tissue or increasing the volume of a biological tissue for cosmetic or therapeutic purposes, comprising administering to a subject in need thereof an effective amount of the injectable dermal filler composition according to claim 1.

13. The method according to claim 12, wherein said cosmetic purposes comprise cosmetic treatment of wrinkles and lines of the skin, glabellar lines, nasolabial folds, chin folds, marionette lines, jawlines, buccal commissures, perioral wrinkles, crow's feet, cutaneous depressions, scars, temples, subdermal support of the brows, malar and buccal fat pads, tear troughs, nose, lips, cheeks, chin, perioral region, infraorbital region, and/or facial asymmetries.

14. The method according to claim 12, wherein said composition is administered to treat stress urinary incontinence, vesicoureteral reflux, vocal fold insufficiency, and/or vocal fold medialization.

* * * * *